United States Patent [19]

Givens et al.

[11] Patent Number: 4,723,022
[45] Date of Patent: Feb. 2, 1988

[54] SUBSTITUTED 2,3-NAPHTHALENEDICARBOXALDEHYDES

[75] Inventors: Richard S. Givens; Robert G. Carlson, both of Lawrence, Kans.; Kasturi Srinivasachar, Rockville, Md.; Takeru Higuchi, Lawrence; Osborne S. Wong, Lenexa, both of Kans.; Richard S. Givens; Robert G. Carlson, both of Lawrence, Kans.; Kasturi Srinivasachar, Rockville, Md.; Takeru Higuchi, Lawrence; Osborne S. Wong, Lenexa, both of Kans.

[73] Assignee: Oread Laboratories, Inc., Lawrence, Kans.

[21] Appl. No.: 837,681

[22] Filed: Mar. 10, 1986

[51] Int. Cl.$^4$ .................. C07D 235/02; C07C 69/76; C07C 59/76; C07C 87/64
[52] U.S. Cl. .................. 548/326; 568/440; 564/428; 564/88; 558/415; 562/462; 556/418; 560/51; 549/433
[58] Field of Search .......... 568/440; 564/428, 88; 558/415; 562/462; 556/418; 560/51; 549/433; 548/326

[56] References Cited

U.S. PATENT DOCUMENTS

| | | | |
|---|---|---|---|
| 3,597,362 | 8/1971 | Bollyky et al. | 562/462 |
| 3,718,432 | 2/1973 | Roth | 562/462 |
| 3,892,530 | 7/1975 | Felix et al. | 562/462 |
| 3,933,430 | 1/1976 | Hare | 562/462 |
| 4,082,773 | 4/1978 | Hauck | 549/433 |
| 4,359,323 | 11/1982 | LePage | 562/462 |

OTHER PUBLICATIONS

Ishida et al., "New Detection and Separation Method for Amino Acids by High-Performance Liquid Chromatography", Journal of Chromatography, 204 (1981), pp. 143-148.
Miura et al., "A Fluorometric Method for the Specific Determination of Serum Arginine with 2,3-Naphthalenedicarbaldehyde", Analytical Biochemistry 139, (1984), pp. 432-437.
Gardner et al., "Reverse-Phase Liquid Chromatographic Analysis of Amino Acids After Reaction with O-Phthalaldehyde", Analytical Biochemistry 101, (1980), pp. 61-65.
Allison et al, "O-Phthalaldehyde Derivatives of Amines for High-Speed Liquid Chromatography/Electrochemistry", Anal. Chem. 56 (1984), pp. 1089-1096.
Miura et al., Chemical Abstracts, vol. 96, No. 65120r, p. 275, (1982), "Fluorometric Method for the Specific Determination of Arginine with 2,3-Naphthalenedicarbaldehyde".
Miyaguchi et al., "Sub-Picomol Chemiluminescence Detection of Dns-Amino Acids Separated by High-Performance Liquid Chromatography with Gradient Elution", Journal of Chromatography, 303 (1984), pp. 173-176.
Kobayashi et al., "Application of High-Performance Liquid Chromatography with Chemiluminescence Detection System to Determine Catecholamines in Urine", Analytical Biochemistry 112, (1981), pp. 99-104.
Miyaguchi et al., "Microbore High-Performance Liquid Chromatography and Chemiluminescence Detection of Dns-Amino Acids", Journal of Chromatography, 316 (1984), pp. 501-505.
Rauhut et al., "Chemiluminescence from Reactions of Electronegatively Substituted Aryl Oxalates with Hydrogen Peroxide and Fluorescent Compounds", Journal of the American Chemical Society, 89:25, (1967), pp. 6515-6522.
Kobayashi et al., "Determination of Fluorescent Compounds by High Performance Liquid Chromatography with Chemiluminescence Detection", Anal. Chem. (1980), 52, pp. 424-427.

Primary Examiner—Henry R. Jiles
Assistant Examiner—Robert C. Whittenbaugh
Attorney, Agent, or Firm—Burns, Doane, Swecker & Mathis

[57] ABSTRACT

A new class of substituted 2,3-naphthalenedicarboxaldehydes (NDA) is disclosed. Such compounds are of the formula:

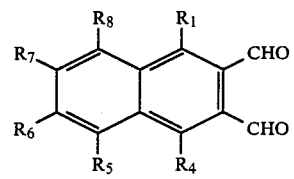

wherein one or more of $R_1$–$R_8$ are various substituting groups. The above compounds react, in the presence of cyanide ion, with compounds containing primary amino groups to form adducts which exhibit a high fluorescent yield and thus are readily detected and measured by fluorometric assaying techniques.

5 Claims, No Drawings

SUBSTITUTED 2,3-NAPHTHALENEDICARBOXALDEHYDES

BACKGROUND OF THE INVENTION i. Field of the Invention

The present invention relates to a fluorometric method for assaying primary amines and more particularly, to a class of compounds which react with primary amines to form fluorescent adducts.

ii. Description of the Prior Art

Assaying techniques wherein a fluorogenic reagent is reacted with a substrate to form a readily detectable fluorescent moiety have been known for some time. One fluorogenic reagent which has been employed for assaying primary amines is o-phthaldehyde (OPA) which is the formula:

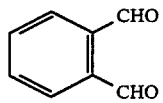

Under mildly alkaline conditions in the presence of a thiol ($R_1SH$) and a primary amine ($RNH_2$), OPA forms 1-alkylthiol-2-alkylisoindole (AAI), which is a fluorescent adduct of the formula:

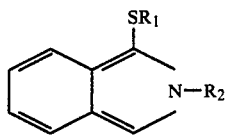

Although the AAI fluorophores generated by the reaction of primary amines and OPA exhibit a relatively high fluorescent intensity with respect to many primary amines, it has been observed that the fluorescent intensity of the isoindole derivatives of primary amines containing an α-amido group are substantially lower. Thus, the OPA/thiol derivatizing system is of limited applicability in the assaying of femtomole quantities of peptides and proteins. Such represents a significant drawback of OPA for assaying many biological systems.

Another problem encountered with fluorogenic assaying techniques employing OPA relates to the relative instability of the 1,2-disubstituted isoindoles of certain amines such as glycine, α-aminobutyric acid and β-alanine. These adducts have been observed to readily degrade into non-fluorescent products thereby placing severe time constraints on analysis.

The o-keto-aldehyde type compounds o-acetylbenzaldehyde (OAB) and o-benzoylbenzaldehyde (OBB), have also been employed as fluorogenic reagents for forming fluorescent adducts (also isoindoles) with primary amines. However, the rate of isoindole formation from OBB is too slow to make it of practical analytical value. OAB forms fluorescent isoindoles more rapidly than OBB and shows improved product stability over those formed with OPA although it is still not completely satisfactory.

SUMMARY AND OBJECTS OF THE INVENTION

In view of the foregoing limitations and shortcomings of prior art techniques for fluorometrically assaying primary amino compounds as well as other disadvantages not specifically mentioned above, it should be apparent that a need still exists in the art for fluorogenic reagents which react rapidly with primary amino compounds to form fluorescent adducts which are both stable and readily detectable. It is, therefore, a primary objective of the present invention to fulfill that need by providing a class of substituted naphthalene dicarboxyaldehydes which, in the presence of cyanide ion and primary amines, form fluorescent adducts which are easily assayed.

It is a further object of this invention to provide a class of substituted naphthalene dicarboxaldehydes which form adducts with primary amino compounds which have good aqueous solubility and long term stability.

Another object of this invention is to provide a class of substituted naphthalene dicarboxaldehydes which form highly fluorescent adducts with primary amino compounds.

Yet another object of this invention is to provide a class of substituted naphthalene dicarboxaldehydes which rapidly form fluorescent adducts with primary amino compounds.

Another object of this invention is to provide a class of substituted naphthalene dicarboxaldehydes which may be employed in the fluorometric assay of primary amino compounds including primary amines, amino acids, peptides and catecholamines.

Briefly described, those and other objects of the invention are accomplished by providing a compound of the formula:

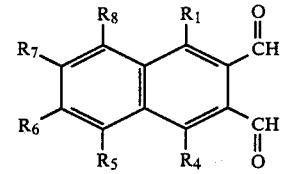

wherein:

(i) $R_1$, $R_5$, $R_6$, $R_7$ and $R_8$ are —H and $R_4$ is —$NO_2$, —$N(CH_3)_2$, —$N(CH_3)_3^+X^-$, —CN, —$CO_2H$, —$CO_2^-M^+$, —$SO_3H$, —$SO_3^-M^+$, —O—Si($CH_3$)$_2$—t—$C_4H_9$, —$OCOCH_3$, —$OCH_2CO_2H$, —$OCH_2CO_2^-M^+$, —$O_2CH$, —$OCH_3$, —OH, or $SO_2NR$ where R is —H or alkyl;

(ii) $R_1$, $R_4$, $R_6$, $R_7$ and $R_8$ are —H and $R_5$ is —$NO_2$, —$N(CH_3)_2$, —$N(CH_3)_3^+X^-$, —CN, —$CO_2H$, —$CO_2^-M^+$, —$SO_3H$, —$SO_3^-M^+$, —O—Si($CH_3$)$_2$—t—$C_4H_9$, —$OCOCH_3$, —$OCH_2CO_2H$, —$OCH_2CO_2^-M^+$, —$O_2CH$, —$OCH_3$, —OH, or $SO_2NR$ wherein R is —H or alkyl;

(iii) $R_1$, $R_4$, $R_5$, $R_7$ and $R_8$ are —H and $R_6$ is —$NO_2$, —$N(CH_3)_2$, —$N(CH_3)_3^+X^-$, —CN, —$CO_2H$, —$CO_2^-M^+$, —$SO_3H$, —$SO_3^-M^+$, —O—Si($CH_3$)$_2$—t—$C_4H_9$, —$OCOCH_3$, —$OCH_2CO_2H$, —$OCH_2CO_2^-M^+$, —$O_2CH$, —$OCH_3$, —OH, or $SO_2NR$ wherein R is —H or alkyl;

(iv) $R_5$, $R_6$, $R_7$ and $R_8$ are —H and $R_1$ and $R_4$, which are identical or different, are —$NO_2$, —$N(CH_3)_2$, —$N(CH_3)_3^+X^-$, —CN, —$CO_2H$, —$CO_2^-M^+$, —$SO_3H$, —$SO_3^-M^+$, —O—Si($CH_3$)$_2$—t—$C_4H_9$, —$OCOCH_3$, —$OCH_2CO_2H$, —$OCH_2CO_2^-M^+$, —$O_2CH$, or $SO_2NR$ wherein R is —H or alkyl;

(v) $R_1$, $R_4$, $R_6$ and $R_7$ are —H and $R_5$ and $R_8$, which are identical or different, are —$NO_2$, —$N(CH_3)_2$, —N(CH$_3$)$_3$+X$^-$, —CN, —CO$_2$H, —CO$_2$—M+, —SO$_3$H, —SO$_3$—M+, —O—Si(CH$_3$)$_2$—t—C$_4$H$_9$, —OCOCH$_3$, —OCH$_2$CO$_2$H, —OCH$_2$CO$_2$—M+, —O$_2$CH, —OCH$_3$, —OH, or SO$_2$NR wherein R is —H or alkyl;

(vi) R$_1$, R$_4$, R$_5$ and R$_8$ are —H and R$_6$ and R$_7$, which are identical or different, are —NO$_2$, —N(CH$_3$)$_2$, —N(CH$_3$)$_3$+X$^-$, —CN, —CO$_2$H, —CO$_2$—M+, —SO$_3$H, —SO$_3$—M+, —O—Si(CH$_3$)$_2$—t—C$_4$H$_9$, —OCOCH$_3$, —OCH$_2$CO$_2$H, —OCH$_2$CO$_2$—M+, O$_2$CH, —OCH$_3$, —OH, or SO$_2$NR wherein R is —H or alkyl; or (vii) R$_1$, R$_4$, R$_5$ and R$_8$ are —H and R$_6$ and R$_7$ are

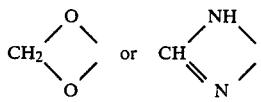

and wherein M+ is a cation and X$^-$ is an anion. Anions and cations are chosen which impart good aqueous solubility to the compounds. Preferably, X$^-$ is a poor nucleophile. Exemplary of M+ cations which may be used according to the invention are Li+, Na+, K+ and R′N+, wherein R is an alkyl group. Exemplary anions X$^-$ are ClO$_4$$^-$, NO$_3$$^-$, CFCO$_2$$^-$, CCl$_3$CO$_2$$^-$ OR HSO$_4$$^-$.

The above compounds are reacted with primary amino compounds in the presence of cyanide ion to form fluorescent adducts.

With the foregoing and other objects, advantages, and features of the invention that will become hereinafter apparent, the nature of the invention may be more clearly understood by reference to the following detailed description of the invention and to the appended claims.

DETAILED DESCRIPTION OF PREFERRED EMBODIMENTS

Various synthetic routes may be followed to prepare the compounds according to the present invention. The starting reagents used in the synthetic routes depicted below are all readily available or may easily be prepared.

(i) Preparation of 5-nitro substituted 2,3-naphthalenedicarboxaldehyde 5-nitro substituted 2,3-naphthalenedicarboxyaldehyde was prepared as follows:

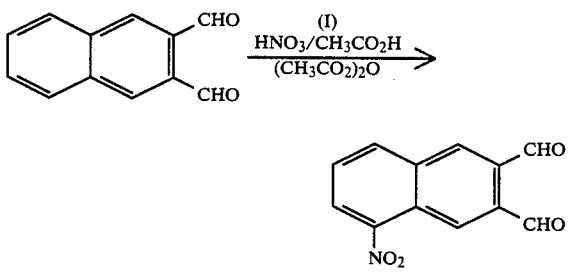

Step I was carried out at 0° C. by mixing the above-described reagents and allowing to stand at room temperature for 40 hours.

The amounts of acetic anhydride, nitric and acetic acid employed per millimole of 2,3-naphthalenedicarboxaldehyde was 1.32 mL nitric acid, 3.9 mL acetic acid and 5.3 mL acetic anhydride.

(ii) Preparation of 5-N,N-dimethylamino naphthalenedicarboxaldehyde

5-N,N-dimethylamino-2,3-naphthalenedicarboxaldehyde was prepared as follows:

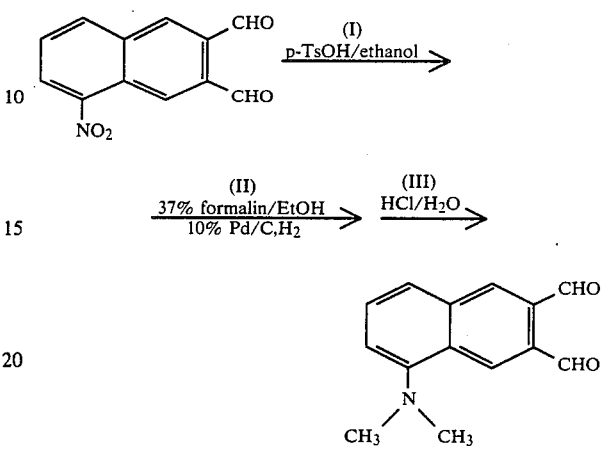

A suspension of 5-nitro-2,3-naphthalene dicarboxaldehyde (1.0 g, 4.37 mmol) in 50 mL of absolute EtOH was converted into the acetal by treating it with a few crystals of p-toluenesulfonic acid. After the reaction mixture became homogeneous the solvent was removed under reduced pressure. The residue was dissolved in EtOH and another crystal of p-toluenesulfonic acid added. After a few minutes the solvent was again removed on a rotary evaporator. The oily residue was dissolved in ether and extracted with saturated aqueous NaHCO$_3$. The organic phase was separated and dried over Na$_2$SO$_4$. Removal of the solvent yielded the acetal as a pale yellow oil which was used without further purification. To a solution of the acetal in 140 mL of ethanol was added 10 mL of aqueous formaldehyde (37%) and 400 mg of 10% Pd/C catalyst. The mixture was hydrogenated until uptake of hydrogen ceased. The catalyst was removed by filtration through Celite and the filtrate was evaporated under reduced pressure. The residue was taken up in ether and extracted with aqueous 1N NaOH solution. The organic phase was separated, washed with brine, dried over K$_2$CO$_3$, and the solvent removed under reduced pressure to give an oily residue. Hydrolysis of the acetal was accomplished by stirring it with 4 mL of 5% aqueous HD1 in 20 mL of acetone overnight at room temperature. After evaporation of the solvent the residue was made basic with 2N aquoeous KOH and extracted with ether. The organic layer was washed with water, dried over MgSO$_4$ and evaporated to yield a dark brown residue which was filtered through a short column of silica gel using methylene chloride for elution. The initial yellow fractions were collected and combined. After removing the solvent the residue was crystallized from methylene chloride-hexane to afford 390 mg (39%) of yellow needles. An analytical sample of 5 was prepared by recrystallization from ether-hexane.

(iii) Preparation of 6,7-methylenedioxa-2,3-naphthalenedicarboxaldehyde:

6,7-methylenedioxa-2,3-naphthalenedicarboxaldehyde was prepared as follows:

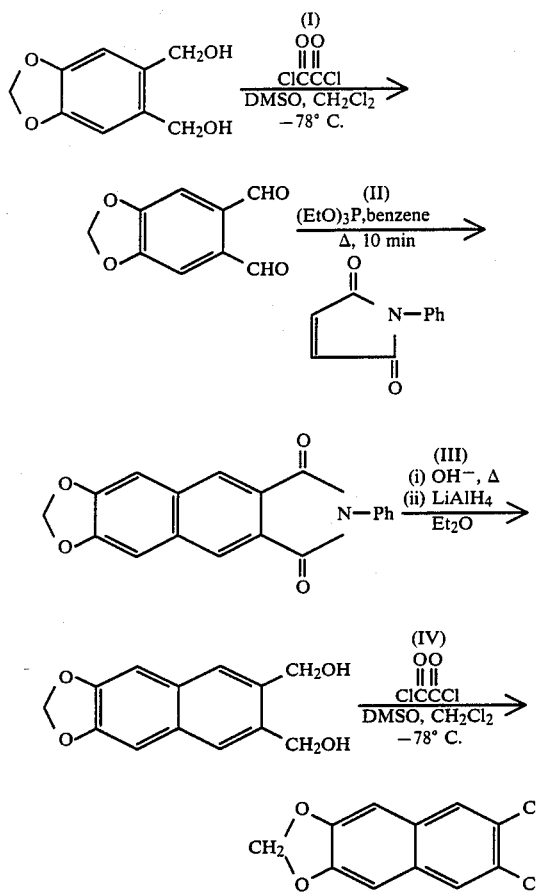

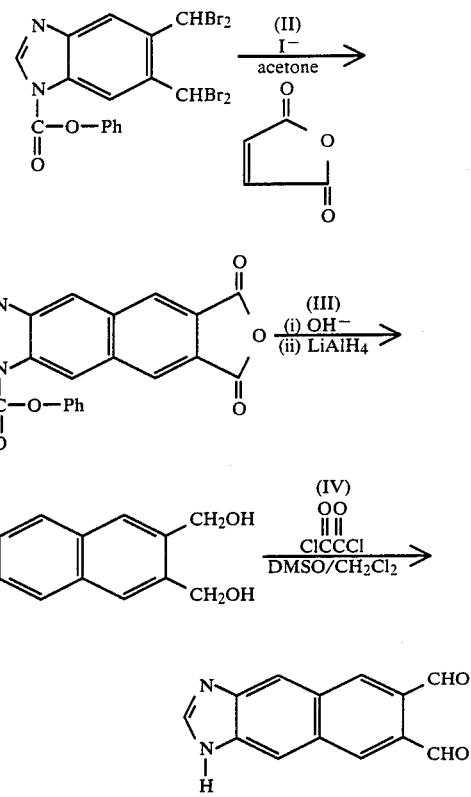

In step I, the diol was combined with dimethylsulfoxide (DMSO) oxalyl chloride, and methylenedichloride at a temperature of −78° C. to form the corresponding dialdehyde. In step II, the dialdehyde was combined with (EtO)₃P, N-phenylmaleimide (in 40% H₂O; 60% MeOH) and benzene and heated for 10 minutes to form an addition product. In step III, the addition product produced in step II was first combined with hydroxide and heated. This was followed by a lithium aluminum hydride reduction in the presence of Et₂O. A three-ringed diol product was thereby produced. Finally, in step (IV) the three-ringed diol product of step (III) was reacted with DMSO and oxalyl chloride at a temperature of −78° C. The 6,7-methylenedioxa-2,3-naphthalene-dicarboxaldehyde product was then recovered.

(iv) Preparation of 1H-naphth[2,3-d]imidazole-6,7-dicarboxaldehyde:

1H-napth[2,3-d]imidazole-6,7-dicarboxaldehyde was prepared as follows:

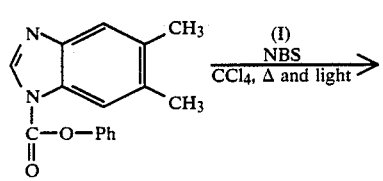

In step I, the dimethyl compound was reacted with N-bromo-succinimide in the presence of CCl₄ and heated (or exposed to light) to produce the corresponding bis-dibromo compound. In step II, the bis-dibromo compound produced in step I was reacted with iodide and maleic anhydride in acetone to produce the anhydride addition product. In step III, the anhydride addition product in step II was first treated with hydroxide and then reduced with LiAlH₄ to produce a dihydroxy addition product. Finally, in step IV the dihydroxy addition product of step III was combined with oxalyl chloride, dimethylsulfoxide and methyldichloride to produce the final dialdehyde product namely, 1H-naphth[2,3-d]imidazole-6,7-dicarboxaldehyde.

(v) Preparation of other monosubstituted 2,3-naphthalenedicarboxaldehydes and 5,8- and 6,7-disubstituted 2,3-naphthalenedicarboxaldehydes:

Monosubstituted 2,3-naphthalenedicarboxaldehydes and 5,8- and 6,7-disubstituted 2,3-naphthalenedicarboxaldehydes may be prepared by employing a starting reagent of the formula:

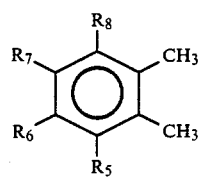

wherein $R_5$, $R_6$, $R_7$ or $R_8$ or $R_5$ and $R_8$ or $R_6$ and $R_7$ are substituted with the moieties desired for the final substituted 2,3-naphthalenedicarboxaldehyde. The above-described substituted benzene is reacted as follows:

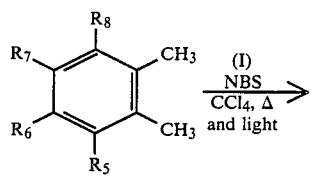

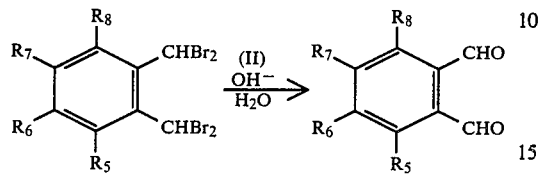

The dialdehyde intermediate produced by step II above may also be produced as follows:

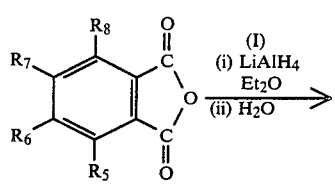

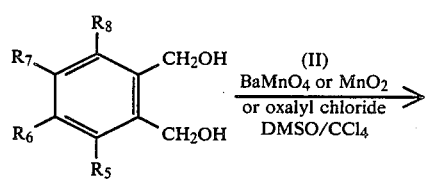

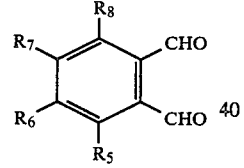

The substituted dialdehydes produced by either of the synthetic routes above are then converted to the corresponding 2,3-naphthalenedicarboxaldehydes as follows:

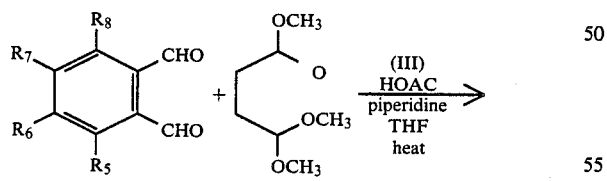

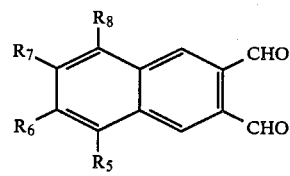

Another synthetic procedure for producing unsubstituted, mono-substituted, and the 5,8- and 6,7 disubstituted 2,3-naphthalenedicarboxaldehydes proceeds as follows:

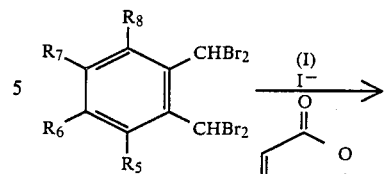

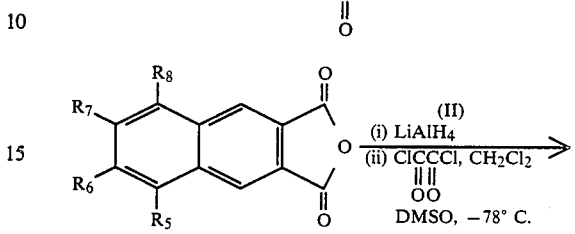

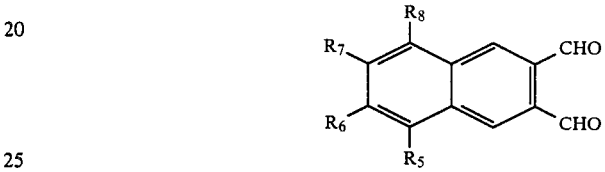

(vi) Preparation of 1,4-disubstituted 2,3-naphthalenedicarboxaldehydes:

1,4-disubstituted 2,3-naphthalenedicarboxaldehydes may be prepared as follows:

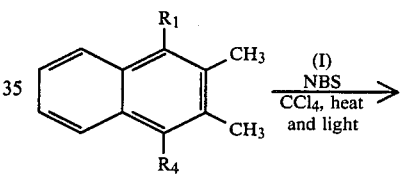

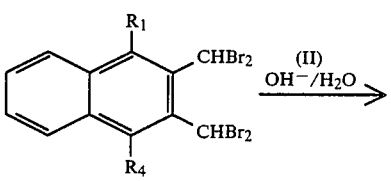

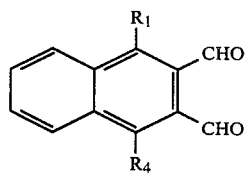

The compounds of this invention react with compounds containing primary amino groups in the presence of cyanide ion to form fluorescent adducts as follows:

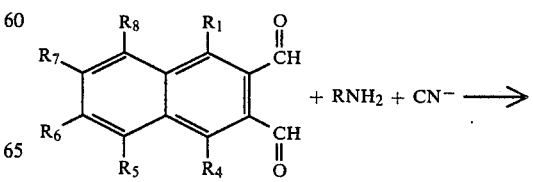

substituted 2,3-naphthalenedicarboxaldehyde

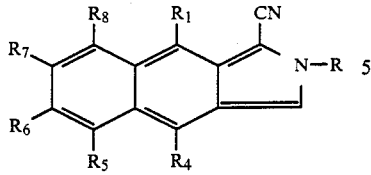

1-cyano-2-alkyl-benz[f]isoindol

The process for forming fluorescent adducts from compounds containing primary amines and 2,3-naphthalenedicarboxaldehyde is described in detail in U.S. patent application Ser. No. 707,676 filed Mar. 4, 1985, the disclosure of which is hereby incorporated by reference.

Typically, the aromatic dialdehydes are reacted with the primary amino compound in the presence of cyanide ion, or a precursor thereof, in a mild alkaline aqueous medium to give a highly stable adduct which is intensely fluorescent. The reaction is carried out at about 30° C. (or room temperature) at a pH ranging from about 9 to about 10.

The fluorometric detection and measurement of primary amino compounds using the substituted 2,3-naphthalenedicarboxaldehydes of the invention is advantageously employed in conjunction with high performance liquid chromatography (HPLC). A mixture of primary amines is derivatized with the inventive compounds in the presence of cyanide followed by HPLC separation and fluorescence detection. Alternatively, a mixture of primary amino compounds is advantageously fractionated by HPLC and the fractionated effluent reacted with the inventive compounds to form the fluorescent adducts.

Although only preferred embodiments are specifically illustrated and described herein, it will be appreciated that many modifications and variations of the present invention are possible in light of the above teachings and within purview of the appended claims without departing from the spirit and intended scope of the invention.

What is claimed is:

1. A compound of the formula:

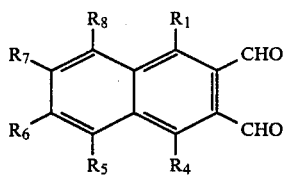

wherein:

(i) $R_1$, $R_5$, $R_6$, $R_7$ and $R_8$ are —H and $R_4$ is —$NO_2$, —$N(CH_3)_2$, —$N(CH_3)_3^+X^-$, —CN, —$CO_2H$, —$CO_2^-M^+$, —$SO_3H$, —$SO_3^-M^+$, —O—Si—$(CH_3)_2$—t—$C_4H_9$, $OCOCH_3$, —$OCH_2CO_2H$, —$OCH_2CO_2^-M^+$, —$O_2CH$, —$OCH_3$, —OH, or $SO_2NR$ wherein R is —H or lower alkyl;

(ii) $R_1$, $R_4$, $R_6$, $R_7$ and $R_8$ are —H and $R_5$ is —$NO_2$, —$N(CH_3)_2$, —$N(CH_3)_3^+X^-$, —CN, —$CO_2H$, —$CO_2^-M^+$, —$SO_3H$, —$SO_3^-M^+$, O—$Si(CH_3)_2$—t—$C_4H_9$, —$OCOCH_3$, —$OCH_2CO_2H$, —$OCH_2CO_2^-M^+$, —$O_2CH$, —$OCH_3$, —OH, or $SO_2NR$ wherein R is —H or lower alkyl;

(iii) $R_1$, $R_4$, $R_5$, $R_7$ and $R_8$ are —H and $R_6$ is —$NO_2$, —$N(CH_3)_2$, —$N(CH_3)_3^+X^-$, —CN, —$CO_2H$, —$CO_2^-M^+$, —$SO_3H$, —$SO_3^-M^+$, —O—$Si(CH_3)_2$—t—$C_4H_9$, —$OCOCH_3$, —$OCH_2CO_2H$, —$OCH_2CO_2^-M^+$, —$O_2CH$, —$OCH_3$, —OH, or $SO_2NR$ wherein R is —H or lower alkyl;

(iv) $R_5$, $R_6$, $R_7$ and $R_8$ are —H and $R_1$ and $R_4$, which are identical or different, are —$NO_2$, —$N(CH_3)_2$, —$N(CH_3)_3^+X^-$, —CN, —$CO_2H$, —$CO_2^-M^+$, —$SO_3H$, —$SO_3^-M^+$, —O—$Si(CH_3)_2$—t—$C_4H_9$, —$OCOCH_3$, —$OCH_2CO_2H$, —$OCH_2CO_2^-M^+$, —$O_2CH$, or $SO_2NR$ wherein R is —H or lower alkyl;

(v) $R_1$, $R_4$, $R_6$, and $R_7$ are —H and $R_5$ and $R_8$, which are identical or different, are —$NO_2$ —$N(CH_3)_2$, —$N(CH_3)_3^+X^-$, —CN, —$CO_2H$, —$CO_2^-M^+$, —$SO_3H$, —$SO_3^-M^+$, —O—$Si(CH_3)_2$—t—$C_4H_9$, —$OCOCH_3$, —$OCH_2CO_2H$, —$OCH_2CO_2^-M^+$, —$O_2CH$, —$OCH_3$, —OH, or $SO_2NR$ wherein R is —H or lower alkyl;

(vi) $R_1$, $R_4$, $R_5$ and $R_8$ are —H and $R_6$ and $R_7$, which are identical or different, are —$NO_2$, —$N(CH_3)_2$, —$N(CH_3)_3^+X^-$, —CN, —$CO_2H$, —$CO_2^-M^+$, —$SO_3H$, —$SO_3^-M^+$, —O—$Si(CH_3)_2$—t—$C_4H_9$, —$OCOCH_3$, —$OCH_2CO_2H$, —$OCH_2CO_2^-M^+$, $O_2CH$, —$OCH_3$, —OH, or $SO_2NR$ wherein R is —H or lower alkyl; or (vii) $R_1$, $R_4$, $R_5$ and $R_8$ are —H and $R_6$ and $R_7$ are

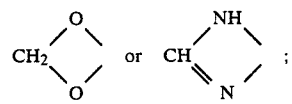

and wherein $M^+$ is a cation and $X^-$ is an anion.

2. The compound of claim 1 of the formula:

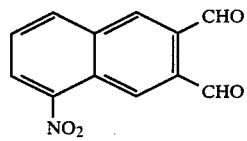

3. The compound of claim 1 of the formula:

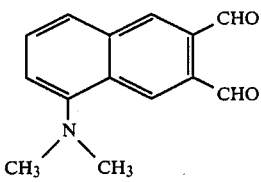

4. The compound of claim 1 of the formula:

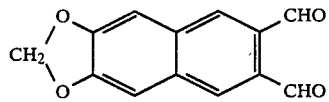

5. The compound of claim 1 of the formula:

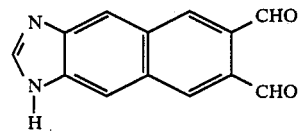

* * * * *